United States Patent [19]

Melgui et al.

[11] Patent Number: 4,647,856

[45] Date of Patent: Mar. 3, 1987

[54] METHOD AND APPARATUS FOR DETERMINING MECHANICAL PROPERTIES OF ARTICLES BY PULSE MAGNETIC METHODS

[75] Inventors: Mikhail A. Melgui; Valery B. Kratirov; Anatoly I. Filippov; Viktor V. Deinekin, all of Minsk, U.S.S.R.

[73] Assignee: Institut Prikladnoi Fiziki Akademii Nauk Belorusskoi SSR, Minsk, U.S.S.R.

[21] Appl. No.: 476,877

[22] PCT Filed: Jul. 28, 1981

[86] PCT No.: PCT/SU81/00063

§ 371 Date: Mar. 22, 1983

§ 102(e) Date: Mar. 22, 1983

[87] PCT Pub. No.: WO83/00560

PCT Pub. Date: Feb. 17, 1983

[51] Int. Cl.[4] .................. G01N 27/72; G01R 33/12
[52] U.S. Cl. .................................. 324/239; 324/228; 324/262
[58] Field of Search ............... 324/222, 223, 239, 243, 324/201, 228, 232, 234, 235, 236, 239

[56] References Cited

U.S. PATENT DOCUMENTS

| | | | |
|---|---|---|---|
| 3,235,795 | 2/1966 | Uozumi | 324/234 |
| 3,586,963 | 6/1971 | Arrott et al. | 324/243 |
| 4,079,312 | 3/1978 | Osborn et al. | 324/226 |

FOREIGN PATENT DOCUMENTS 1076168 7/1967 United Kingdom .
728068 12/1979 U.S.S.R. .
790281 12/1980 U.S.S.R. .

OTHER PUBLICATIONS

M. A. Melguy, "A Pulse-Local Magnetic Method of Controlling the Mechanical Properties of Steels," Nauki i tekhnika, 1980, p. 140.
Forster et al, "Die schnelle zerstorungsfreie Bestimmung der Blechanisotropie mit dem Restpunktpolverfahren," Zeitschrift fur metalkunde, Bd 45, H 4, 245, 1954.
"Defectoskopiya", 1979, No. 3, p. 29.

Primary Examiner—Ernest F. Karlsen
Assistant Examiner—Walter E. Snow
Attorney, Agent, or Firm—Fleit, Jacobson, Cohn & Price

[57] ABSTRACT

A method comprises repeatedly magnetizing a test article by a pulsed axially symmetric magnetic field normal to the surface of the test article, and reading the gradient of a residual field. Magnetizing the article is effected by two trains of pulses in two steps: first until a first instant of discontinuance in the growth of the gradient of a remanent magnetic field and then until a second instant of discontinuance, the pulse amplitude of the second pulse train being lower than a maximum amplitude of the second pulse train.

An apparatus to carry out the proposed method comprises a pulse shaper 1 for forming pulses of an axially symmetric magnetic field and a measuring circuit for measuring the gradient of a remanent field normal component. According to the invention said apparatus is further provided with a working storage 4, a comparison circuit 5 and a pulse amplitude measuring device 2 for measuring pulse amplitude at the output of the pulse shaper 1. The amplitude measuring device 2 has its inputs connected to the outputs of the comparison circuit 5 and the pulse shaper 1. The inputs of the working storage 4 and the comparison circuit 2 are connected to the output of the gradient measuring circuit 3. The other input of the comparison circuit 5 is connected to the output of the working storage 4. The pulse shaper 1 includes a storage capacitor, charging and discharging circuits of said capacitor, an inhibit circuit and a comparison circuit, a pulse counter, a decoder and a code-to-analog converter electrically connected to one another.

4 Claims, 3 Drawing Figures

METHOD AND APPARATUS FOR DETERMINING MECHANICAL PROPERTIES OF ARTICLES BY PULSE MAGNETIC METHODS

TECHNICAL FIELD

The invention relates to the practice of a non-destructive testing of articles made from ferromagnetic materials, and particularly to a method and apparatus for determining mechanical properties of an article made from ferromagnetic material.

BACKGROUND ART

Known in the art is a method for determining mechanical properties of articles made from ferromagnetic materials (cf. Förster, Zeitschrift für Metalkunde, Bd 45, H 4, 245, 1954), in which the test article is magnetized through a single exposure to an axially symmetric magnetic field normal to the surface of said article. Mechanical properties of the article being tested are determined by the magnitude of the tangential component of a local magnetic field of remanent magnetization. The method is carried out with the aid of a device wherein as a magnetizing means use is made of a linear permanent magnet.

However, the results obtained through a single magnetization are not stable and therefore cannot be reproduced unless the article being examined is demagnetized before a repeated measurement is made. Besides, said device is highly sensitive to a gap between the permanent magnet and the article, and to a structural anisotropy of the material from which the article is fabricated.

There is also known a method for determining mechanical properties of articles made from ferromagnetic materials (cf. Melgui M. A. "Magnitny kontrol mehanitcheskih svoistv staley", Nauka i tekhnika, 1980, p. 140), wherein the test article is magnetized by repeatedly exposing it to a pulsed axially symmetric magnetic field having a constant amplitude. The symmetry axis of said magnetic field is maintained normal to the surface of the article. Then the normal component gradient of the magnetic field of remanent magnetisation is determined along the symmetry axis of said magnetic field with the aid of a ferroprobe-gradiometer. The method rules out the influence of the magnetic history in the case of thin articles and provides for stable results in testing such articles.

However, indefinitness of the depth of magnetization in the case of articles having a greater thickness and the influence of the magnetic history of such articles affect the stability and precision of the testing results. For the above reasons this method cannot be used for testing such articles as, for instance, rolled plates thicker than 4 mm.

A device for carrying out the above method (cf. "Defectoskopiya", 1979, No. 3, p. 29) comprises a pulse shaper adapted to form pulses of an axially symmetric magnetic field, a circuit for measuring a gradient of remanent magnetization, and an indicator, all the above elements connected in series. The pulse shaper is contructed in the form of a magnetizing device (solenoid) connected to a conventional current pulse generator.

Magnetizing the test article is effected by the pulses of the solenoid magnetic field. The solenoid is installed so that its end face is adjacent to the surface of the test article. A signal from a transducer adapted to convert a gradient of the normal component of remanent magnetization to electric signals is applied to the measuring circuit from which it is transmitted to the indicator. The readings of the indicator are used for determining mechanical properties of the article being examined.

The above apparatus provides for reliable test results in testing articles having a thickness less than 4 mm. However, in controlling the quality of a product after a thermal treatment and determining mechanical properties of articles having a greater thickness, the recurrence and, hence the reliability and precision provided by such quality control are lower.

DISCLOSURE OF INVENTION

The invention is directed to the provision of a method and apparatus for determining mechanical properties of articles made from ferromagnetic materials, which due to improvements in conditions of and means for magnetizing the test article, allow the precision and reliability of the test results to be enhanced in a wide range of thickness of the articles being tested.

The object of the invention is attained in a method for determining mechanical properties of articles made from ferromagnetic materials, which comprises repeatedly magnetizing the article by an axially symmetric magnetic field whose symmetry axis is maintained at the zone of magnetization perpendicular to the surface of the article reading the values of the remanent local field gradient along said symmetry axis, and determining the mechanical properties of the article by the magnitude of said gradient, and wherein according to the invention the article is magnetized by a first train of pulses until a first instant of discontinuance in the growth of the remanent magnetic field gradient, and then by a second train of pulses until a second instant of discontinuance in the growth of said remanent magnetic field gradient, the pulse amplitude of the second pulse train being lower than the maximum amplitude of pulse of the first pulse train.

The object of the invention is further achieved by gradually increasing the pulse amplitude of the first pulse train until the first instant of discontinuance in the growth of the remanent magnetic field gradient occurs, and gradually decreasing the pulse amplitude of the second pulse train until the second instant of discontinuance in the growth of said remanent magnetic field gradient occurs.

The object of the invention is also attained in a an apparatus for determining mechanical properties of articles made from ferromagnetic materials, which comprises a pulse shaper for forming pulses of an axially symmetric magnetic field and a measuring circuit for measuring the gradient of a remanent field normal component, and wherein according to the invention there are further provided a working storage for storing measured values of said gradient for a time interval between pulses, a comparison circuit for comparing two successive signals at the output of said gradient-measuring circuit and said working storage, and a pulse amplitude measuring device at the output of said pulse shaper, said pulse amplitude measuring device having its inputs connected to the output of the comparison circuit and to the comparison circuit and to the output of said pulse shaper, the working storage and the comparison circuit having their inputs connected to the output of the gradient measuring circuit, the other input of the comparison circuit being connected to the output of the working storage, and the input of the pulse shaper being connected to the output of the comparison circuit, the pulse shaper for forming pulses of an axially symmetric magnetic field includes a storage capacitor with a charging circuit connected in series thereto and having a resistor connected in series with a controlled gate, and also a discharging circuit of said storage capacitor, having a magnetizing device connected in series with a controlled gate, an inhibit circuit of the controlled gate in the charging circuit, a comparison circuit having its one input connected to the point of connection of the charging and discharging circuits to the storage capacitor, and its output connected to the inhibit circuit of the controlled gate in the charging circuit, to a control electrode of the gate in the discharging circuit, and also to a count input of a magnetizing pulse counter, the output of said counter being connected through a decoder to the input of a code-to-analog converter having its one output connected to the control electrode of the gate in the charging circuit and its other output connected to the second input of the comparison circuit.

The above-described method and apparatus permit magnetizing the article to such a state where the gradient of a residual local field does not change even when the magnetization current is increased. The method makes it possible to select an optimum amplitude of the magnetization current depending, for instance, on the quality of a steel, from which a test article is made or the thickness thereof. A discontinuance in the growth and a subsequent decrease in the residual magnetization field and its gradient with the increase of the amplitude of the magnetization field pulses, which has been established experimentally, renders it possible to eliminate at an optimum amplitude of said pulses the influence of the magnetic history of the test article.

BRIEF DESCRIPTION OF DRAWINGS

The invention will now be explained in greater detail with reference to embodiments thereof which are represented in the accompanying drawings, wherein.

BEST MODE OF CARRING OUT THE INVENTION

Figure 1:
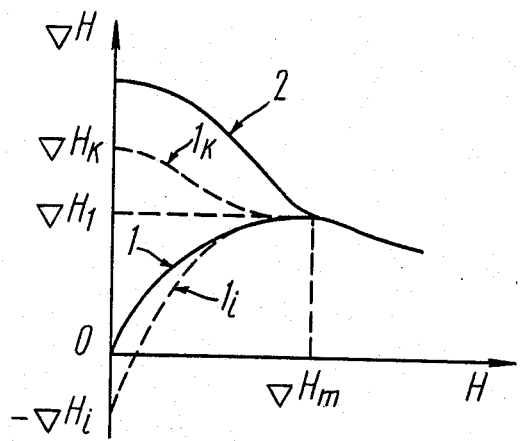
FIG. 1 represents a curve of a normal component of remanent magnetization field or of its gradient depending on the pulsed magnitization field magnitude according to the invention.
Figure 2:
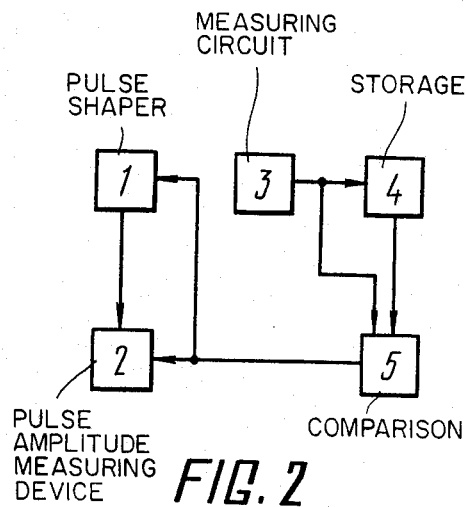
FIG. 2 represents a block diagram of the proposed apparatus.

Referring now to FIG. 2, the proposed apparatus comprises a pulse shaper 1 of an axially symmetric magnetic field, a pulse amplitude measuring device 2, a measuring circuit 3 for measuring the gradient of a residual field normal component, a storage 4, a comparison circuit 5. The output of the pulse shaper 1 is connected to the pulse amplitude measuring device 2. The output of the measuring circuit 3 is connected to the inputs of the storage 4 and of the comparison circuit 5, said comparison circuit 5 having its second input connected to the output of the storage 4. The comparison circuit 5 has its output connected to a second input of the pulse amplitude measuring device 2 and also to the input of the pulse shaper 1.

Figure 3:
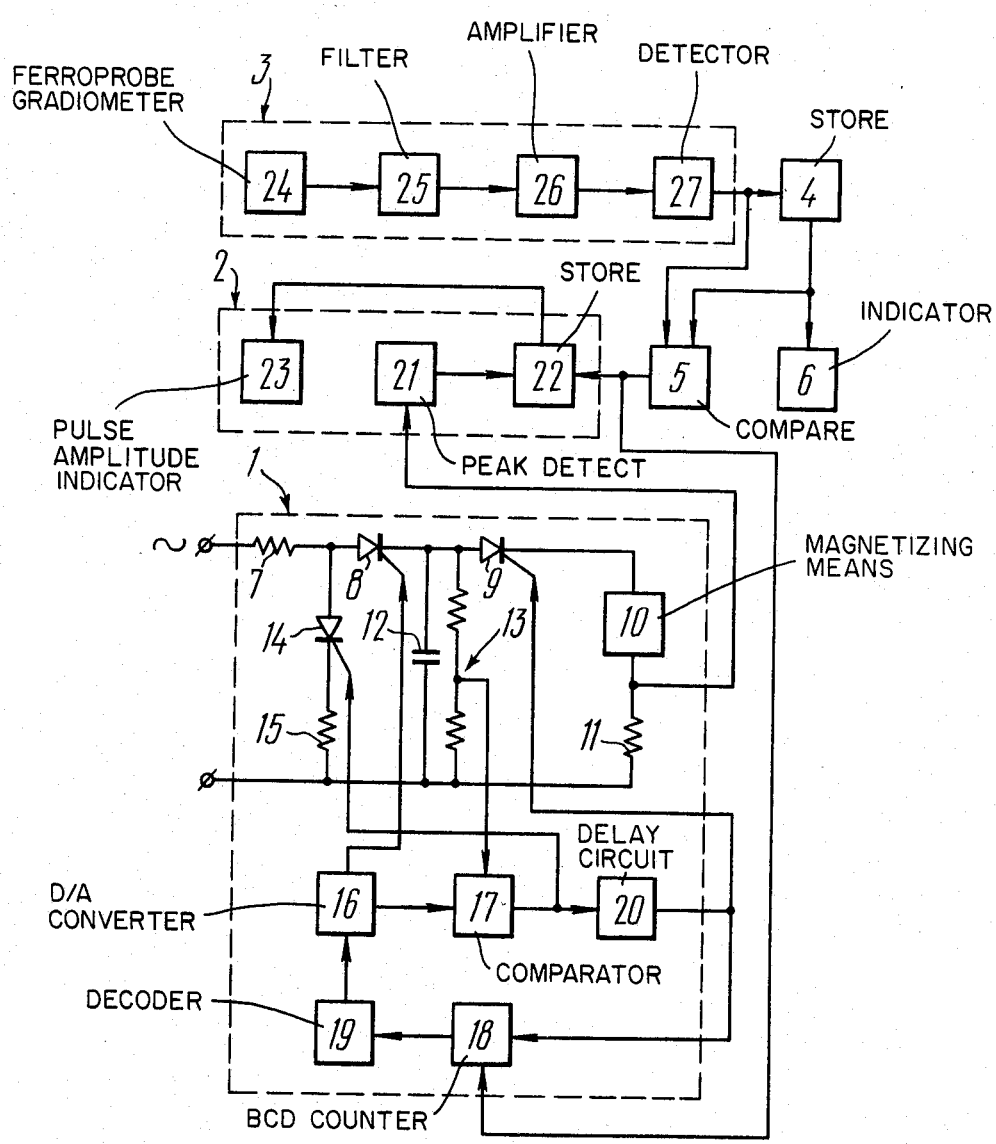
FIG. 3 represents a detailed block diagram of the apparatus shown in FIG. 2.

Shown in FIG. 3 is a possible modification of the proposed apparatus connected to an indicator 6.

The pulse shaper 1, which is adapted to form pulses of an axially symmetric magnetic field, comprises a charging circuit including a resistor 7 and a controlled gate 8 connected in series to said resistor, a discharging circuit including a controlled gate 9, a magnetizing means 10 (in the form of a solenoid), and a resistor 11. The apparatus further includes a storage capacitor 12 and resistor-type voltage divider 13 connected in parallel with said storage capacitor, an inhibit circuit of the gate 8, which includes a controlled gate 14 and a resistor 15, a code-to-analog converter 16, a comparison circuit 17, a binary coded decimal counter (BCD counter) 18, a decoder 19 and a delay circuit 20.

One input of the comparison circuit 17 is connected to the resistor-type voltage divider 13, a second input of the comparison circuit 17 is connected to one of the outputs of the code-to-analoge converter 16, and the output of said comparison circuit 17 is connected to a control electrode of the controlled gate 14 in said inhibit circuit of the gate 8 and to an input of the delay circuit 20. The output of said delay circuit 20 is connected to a control electrode of the controlled gate 9 in said discharging circuit and to a count input of the BCD counter 18 having its output connected through the decoder 19 to the input of the code-to-analog converter 16 having its output connected to the control electrode of the gate 8.

The pulse amplitude measuring device 2 includes a peak detector 21 and a storage 22 connected in series to said detector. Connected to the storage 22 is a pulse amplitude indicator 23. The gradient-measuring circuit 3 comprises a series circuit including a ferroprobe-gradiometer 24, a filter 25, an amplifier 26, and a detector 27.

The resistor 11 of the pulse shaper 1 is connected to the peak detector 21, and the output of the detector 27 is connected to the input of the storage 4 and of the comparison circuit 5 having its output connected to the input of the storage 22 and also to the binary coded decimal counter 18.

Shown in FIG. 3 is a preferred embodiment of the invention. However, various modifications may be made in the invention without departing from the spirit thereof as defined in the claims.

Thus, for instance, the input of the comparison circuit 17 may be connected directly to the point of connection of the charging and discharging circuits with the storage capacitor 12. Further, the storage capacitor may be constructed in the form of several capacitors connected in series to one another, with the input of the comparison circuit 17 connected between said capacitors. Also, the inhibit circuit of the gate 8 may be otherwise variously constructed depending on the type of said gate.

The proposed apparatus operates in the following manner.

The storage capacitor 12 is charged from an a.c. supply through the charging circuit composed of the resistor 7 and the gate 8. The gate 8 is controlled with the aid of the code-to-analog converter 16 having its input connected to the output of the decoder 19 connected to the output of the binary coded decimal counter 18. When the pulse shaper 1 is energized the BCD counter 18 is set to its initial state. The output of the BCD counter, representative of the state of the counter, is coded by the decoding circuit 19, while the code-to-analog converter 16 supplies a reference voltage to the comparison circuit 17, and simultaneously a gating signal from its output is applied to the gate 8 in the charging circuit, thereby rendering said gate conducting. The storage capacitor 12 is charged to a voltage predetermined by the code-to-analog converter 16.

When the predetermined voltage is attained the comparison circuit 17 operates to generate an inhibit pulse rendering the gate 8 in the charging circuit nonconducting, which inhibit pulse is applied to the gate 14 of the inhibit circuit and charging the storage capacitor 12 is interrupted. Simultaneously a signal is applied to the delay circuit 20 from the output of which a signal is applied to the gate 9 in the discharging circuit and to the BCD counter 18, thereby allowing the storage capacitor 12 to discharge and causing the counter 18 to start counting the magnetization pulses. After the storage capacitor has been discharged its charging is repeated, but the output voltage of the code-to-analog converter 16, applied to the comparison circuit 17, will be determined now by a new state of the counter. By employing various types of the binary coded decimal counters 18 and decoders 19 it is possible to obtain any desirable law of the reference voltage variation at the output of the code-to-analog converter 16, and hence a law of charging the storage capacitor 12, which law determines a law of the magnetization pulse amplitude variation. The amplitude of each pulse in one train of pulses is strictly defined. For instance, in the case of a four-digit binary revercible counter it is possible to obtain 15 various output voltages of the code-to-analog converter 16 by decoding the contents of said counter in a code 1-2-4-8, first said voltages are arranged in increasing order of magnitude and then in decreasing order, and thus to provide magnetizing of the test article by magnetic field pulses first of increasing and then of decreasing amplitude. The gates used may be thyristors, thyratrons, magnetrons and other controlled gates.

When a current pulse is passed through the magnetizing solenoid 10, a voltage from the resistor 11 is applied to the peak detector 21 of the amplitude measuring device 2. As the amplitude measuring device use may be made of Hall generator. Alternatively, said voltage may be derived from an additional winding of the solenoid 10. From the peak detector 21 the signal is transmitted to the storage 22 from whose output said signal is applied to the indicator 23.

The test article is magnetized by the magnetizing solenoid 10 when a current pulse passes therethrough. The gradient of the residual field normal component is measured by the ferroprobe-gradiometer 24, then a second harmonic of e.m.f. of the ferroprobe 24 is selected by the filter 25, whereafter said harmonic is amplified by the amplifier 26, detected by the detector 27, and applied to the storage 4. Simultaneously, the thus rectified signal is applied to the comparison circuit 5. The comparison circuit 5 compares the actual signal being measured with the previous one withdrawn from the storage 4. If said signals are equal, the comparison circuit 5 forms a signal which is applied to the storage 22 of the amplitude measuring device, which stores the last pulse amplitude of the axially symmetric magnetic field. Simultaneously, a signal applied from the comparison circuit to the counter 18 causes the latter to reverse. The impulse shaper 1 generates a train of pulses having an amplitude decreasing to zero. To repeat the measurements the whole measurement procedure must be also repeated.

The measurement results are transmitted from the storage 4 to the indicator 6. Since the pulse repetition frequency is controlled by a delay time, the time-delay circuit 20 is preferably used only when there is a need to change the frequency of repetition of the magnetization pulses.

When magnetizing of the demagnetized test article is effected by a train of pulses having increasing amplitude, the gradient of the magnetic field resulting from remanent magnetization increases according to curve 1 to assume a given maximum value which corresponds to the first instant of discontinuance in the growth of the gradient, whereafter said gradient starts decreasing due to eddy currents. The gradient value $\nabla H_1$ at this first instant determines a maximum amplitude of the pulse train. On the following exposure of the test article to the pulses of the magnetic field, with said pulses having an amplitude decreasing to zero, the gradient of the magnetic field caused by the remanent magnetization considerably increase according to curve 2. The pattern of changes in said gradient represented by curve 2 has been established by us as a result of a research work associated with the present invention.

The gradient value $\nabla Hm$ is obtained at a second instant, its growth terminates and it can be measured to a high degree of precision, thereby allowing a more accurate determination of mechanical properties of the test article.

If at the beginning the test article has a certain quantity of negative magnetization with a gradient value being $\nabla Hi$, then on the exposure of said article to a train of pulses having an amplitude decreasing to the same value Hm, the gradient of the field caused by the remanent magnetization, changing according to curve 1, will be $\nabla H_1$, and on the exposure to a train of pulses of a decreasing amplitude, said gradient will assume $\nabla Hm$.

If at the begining the test article has a positive magnetization+Hk, the gradient of the magnetic field caused by remanent magnetization will change under the action of a train of pulses having an increasing amplitude, according to curve 1k, to assume $\nabla H_1$, and under the following action of a train of pulses having a decreasing amplitude, said gradient will be increasing according to curve 2 to assume value $\nabla Hm$. This suggests that irrespective of the magnetic history of the test article, the value $\nabla Hm$ thus obtained is determined only by a maximum amplitude of the magnetic field, which amplitude depends on the structure of the material from which the test article is made, that is on its mechanical properties.

EXAMPLE 1

A 18 mm hot-rolled plate manufactured from a structural steel with a carbon content of 0.32 to 0.40% was tested for mechanical properties. To this end said plate, which had been previously demagnetized, was magnetized by a train of pulses of an axially symmetric field, said pulses having an increasing amplitude. The number of pulses in the pulse train was 15. The initial amplitude was $1 \times 10^5$ a/m, and the final amplitude was $1.5 \times 10^6$ a/m.

A stable value $\Delta H_1$ of the first gradient of the remanent magnetic field was $3.6 \times 10^3$ A/m².

After the above first gradient value had been obtained, magnetizing the test article was continued by a train of pulses having an amplitude decreasing to zero. The number of pulses in this pulse train was 15, and the resulting second or measurement gradient $\nabla Hm$ was $9.3 \times 10^3$ A/m². With a known correlation dependence between said measurement gradient and any individual property of the test material, to say ultimate strength $\sigma_B$, said measurement gradient value corresponds to 58 kg/mm² accurate to 2 kg/mm².

EXAMPLE 2

A 18 mm hot-rolled plate manufactured from a steel of a similar quality as in Example 1 was tested for mechanical properties.

The plate was magnetized in its initial state to $\nabla Hi = -2.8 \times 10^3$ A/m$^2$. The magnetization was effected with the aid of train of pulses as in Example 1. A stable value $\nabla H_1$ of the residual field gradient was $3.6 \times 10^3$ A/m$^2$. The magnetization operation was then carried out in a similar way as disclosed in Example 1. The measurement gradient value $\nabla Hm$ obtained on completion of this train of pulses was $9.29 \times 10$ A/m$^2$, which gradient value with a known correlation dependence between the remanent magnetic field gradient and, for instance, ultimate strength $\sigma_B$ corresponds to 58 kg/mm$^2$ accurate to 2 kg/mm$^2$.

EXAMPLE 3

A 18 mm hot-rolled plate manufactured from a steel of a similar quality as in Example 1 was tested for mechanical properties.

At the initial state the plate was magnetized to $\nabla Hk = 4.2 \times 10^3$ A/m$^2$. whereafter the method was carried out in a similar way as in Example 1. The following values were obtained: $\nabla H_1 = 3.6 \times 10^3$ A/m$^2$, and $\nabla Hm = 9.31 \times 10^3$ A/m$^2$, which corresponds to an ultimate strength $\sigma_B = 58$ kg/mm$^2$ accurate to 2 kg/mm$^2$.

A higher sensitivity and accuracy of measurement can also be obtained under other conditions of magnetization such as, for instance, at a constant amplitude of pulses of the first pulse train, at a constant amplitude of pulses of the second pulse train, at a constant amplitude of pulses of the first pulse train and a decreasing amplitude of pulses of the second train. However, the above-described embodiment of the proposed method allows the consumption of energy to be reduced as compared to the other modifications and therefore is preferable.

The use of the proposed method and apparatus for controlling the quality of a thermal treatment and determining mechanical properties of articles made of ferromagnetic materials allows improving the accuracy and reproducibility of the test results.

INDUSTRIAL APPLICABILITY

The invention may be used in the devices for controlling the quality of a thermal treatment and determining mechanical properties of articles made of ferromagnetic materials.

We claim:

1. A method for determining mechanical properties of a test article made of ferromagnetic materials, comprising the steps of:
    repeatedly magnetizing the test article by a pulsed axially symmetric magnetic field whose symmetry axis at the zone of magnetization is maintained perpendicular to the surface of the article;
    reading gradient values of a remanent local field along said symmetry axis; and,
    determining mechanical properties of the test article by the magnitude of said gradient;
    the repeated magnetizing of the test article including the steps of:
    magnetizing the test article by a first train of pulses until a first instant of discontinuance in the growth of said gradient; and then,
    magnetizing the test article by a second train of pulses until a second instant of discontinuance in the growth of said gradient, the pulse amplitude of the second pulse train being lower than the maximum amplitude of pulses of the first pulse train;
    the mechanical properties of the test article being determined based upon the measured magnitude of said gradient until said second instant.

2. A method as claimed in claim 1, wherein the pulse amplitude of the first pulase train is gradually increased until the first instant of discontinuance in the growth of the remanent magnetic field gradient, and the pulse amplitude of the second pulse train is gradually decreased until the second instant of discontinuance in the growth of the remanent magnetic field gradient.

3. A device for determining mechanical properties of an article made of a ferromagnetic material, comprising:
    a pulse shaper for forming pulses of an axially symmetric magnetic field and having an output;
    a measuring circuit for measuring a gradient of a remanent field normal component;
    a working storage coupled to the gradient measuring circuit for storing measured values of said gradient for a time interval between pulses,
    a comparison circuit for comparing two successive signals at the output of the gradient measuring circuit and said working storage and having an output; and,
    a pulse amplitude measuring device having one input coupled to the output of said pulse shaper and having another input coupled to the output of the comparison circuit;
    the pulse shaper having an input coupled to the output of said comparison circuit, and including:
    a storage capacitor;
    a charging circuit connected in series to said storage capacitor and having a resistor connected in series with a first controlled gate, said first controlled gate having a first control electrode;
    a discharging circuit coupled to said storage capacitor, said discharging circuit including a second controlled gate connected in series with a magnetizing device, said second controlled gate having a second control electrode;
    an inhibit circuit having an input connected to said storage capacitor, said inhibit circuit connected to said first control electrode of the first controlled gate in the charging circuit and connected to the second control electrode of the second controlled gate in the discharging circuit;
    a magnetizing pulse counter coupled to an output of said inhibit circuit;
    a decoder coupled to the pulse counter and having an output;
    the inhibit circuit including: a code-to-analog converter coupled to the decoder output and having an output connected to the first control electrode of the first controlled gate in the charging circuit, said code-to-analog converter having another output connected to an input of a comparator circuit, the other input of said comparator circuit being connected to said storage capacitor.

4. A device for determining mechanical properties as claimed in claim 3 wherein said inhibit circuit includes a third controlled gate having a third control electrode and a second resistor serially coupled to said third controlled gate, said comparator circuit having an output connected to said third control electrode of said inhibit circuit and to said second control electrode of said discharge circuit and said magnetizing pulse counter.

* * * * *